(12) United States Patent
Strebelle et al.

(10) Patent No.: US 7,667,084 B2
(45) Date of Patent: *Feb. 23, 2010

(54) PROCESS FOR THE MANUFACTURE OF 1,2-DICHLOROETHANE

(75) Inventors: Michel Strebelle, Brussels (BE); Dominique Balthasart, Brussels (BE)

(73) Assignee: SOLVAY(Societe Anonyme), Brussels (BE)

( * ) Notice: Subject to any disclaimer, the term of this patent is extended or adjusted under 35 U.S.C. 154(b) by 172 days.

This patent is subject to a terminal disclaimer.

(21) Appl. No.: 11/722,587

(22) PCT Filed: Dec. 21, 2005

(86) PCT No.: PCT/EP2005/057049

§ 371 (c)(1), (2), (4) Date: Oct. 17, 2007

(87) PCT Pub. No.: WO2006/067193

PCT Pub. Date: Jun. 29, 2006

(65) Prior Publication Data

US 2008/0207965 A1 Aug. 28, 2008

(30) Foreign Application Priority Data

| Dec. 23, 2004 | (FR) | 04 13873 |
| Apr. 1, 2005 | (FR) | 05 03252 |
| Apr. 1, 2005 | (FR) | 05 03258 |

(51) Int. Cl.
 C07C 17/15 (2006.01)
 C08F 2/00 (2006.01)

(52) U.S. Cl. .......... 570/223; 570/224; 526/62

(58) Field of Classification Search ........... 570/223, 570/224; 526/62
 See application file for complete search history.

(56) References Cited

U.S. PATENT DOCUMENTS

| 5,789,499 A * | 8/1998 | Masuko et al. ............ 526/62 |
| 6,900,363 B2 * | 5/2005 | Harth et al. ............... 570/223 |
| 2004/0267063 A1 * | 12/2004 | Harth et al. ............... 570/224 |
| 2007/0142682 A1 | 6/2007 | Strebelle et al. |
| 2007/0161830 A1 | 7/2007 | Strebelle |
| 2009/0203854 A1 | 8/2009 | Strebelle et al. |

FOREIGN PATENT DOCUMENTS

| GB | 1 207 767 | 10/1970 |
| WO | 00 26164 | 5/2000 |
| WO | 03 044125 | 5/2003 |
| WO | 03 048088 | 6/2003 |

OTHER PUBLICATIONS

Heinz Zimmermann, et al., "Ethylene", Ullmann's Encyclopedia of Industrial Chemistry, XP 002356911, pp. 1-47, 2000.
U.S. Appl. No. 11/722,603, filed Jun. 22, 2007, Strebelle, et al.
U.S. Appl. No. 11/722,589, filed Jun. 22, 2007, Balthasart, et al.
U.S. Appl. No. 11/722,598, filed Jun. 22, 2007, Strebelle, et al.
U.S. Appl. No. 11/722,607, filed Jun. 22, 2007, Strebelle, et al.
U.S. Appl. No. 12/304,297, filed Dec. 11, 2008, Balthasart, et al.
U.S. Appl. No. 12/304,329, filed Dec. 11, 2008, Strebelle, et al.
U.S. Appl. No. 12/304,379, filed Dec. 11, 2008, Balthasart, et al.

* cited by examiner

Primary Examiner—Jafar Parsa
(74) Attorney, Agent, or Firm—Oblon, Spivak, McClelland, Maier & Neustadt, L.L.P.

(57) ABSTRACT

Process for the manufacture of 1,2-dichloroethane starting with a hydrocarbon source according to which: a) the hydrocarbon source is subjected to a first cracking step, namely a pyrolysis step performed in a cracking oven, thus producing a mixture of cracking products; b) the said mixture of cracking products is subjected to a succession of treatment steps ending with a drying step which makes it possible to obtain a mixture of products containing ethylene and other constituents; c) the said mixture of products containing ethylene derived from step b) is separated into at least one fraction containing ethylene and into a heavy fraction; d) the fraction (s) containing the ethylene is (are) conveyed to a chlorination reactor and/or to an oxychlorination reactor, in which reactors most of the ethylene present is converted to 1,2-dichloroethane; e) the 1,2-dichloroethane obtained is separated from the streams of products derived from the chlorination and oxychlorination reactors; the process being characterized in that a step for hydrogenating the acetylene is carried out upstream of the drying step ending the succession of treatment steps constituting step b) and/or on at least one of the fractions containing ethylene after separation during step c).

16 Claims, 1 Drawing Sheet

PROCESS FOR THE MANUFACTURE OF 1,2-DICHLOROETHANE

This application is a 371 of PCT/EP2005/057049 filed Dec. 21, 2005.

The present invention relates to a process for the manufacture of 1,2-dichloroethane (DCE), a process for the manufacture of vinyl chloride (VC) and a process for the manufacture of polyvinyl chloride (PVC).

To date, ethylene which is more than 99.8% pure is normally used for the manufacture of DCE essentially intended for the manufacture of VCM. This ethylene of very high purity is obtained via the cracking of various petroleum products, followed by numerous complex and expensive separation steps in order to isolate the ethylene from the other products of cracking and to obtain a product of very high purity.

Given the high cost linked to the production of ethylene of such high purity, various processes for the manufacture of DCE using ethylene having a purity of less than 99.8% have been developed. These processes have the advantage of reducing the costs by simplifying the course of separating the product resulting from the cracking and by thus abandoning complex separations which are of no benefit for the manufacture of DCE. For example, patent application WO 03/48088 describes a process for the manufacture of DCE by dehydrogenation of ethane, giving rise to the formation of a fraction comprising ethane, ethylene and impurities including hydrogen, which fraction is then subjected to chlorination and/or oxychlorination.

Among the impurities present in the fraction containing ethylene having a purity of less than 99.8% which is derived from such processes, is also acetylene whose presence during the chlorination and oxychlorination reactions causes problems of exploitation. Indeed, the presence of acetylene during these reactions causes the formation of by-products which are, on the one hand, non-upgradable and, on the other hand, contribute to soiling the equipment. As the formation of these by-products needlessly consumes the reagents such as chlorine, this moreover puts a strain on the yield of the chlorination/oxychlorination reactions. Among the by-products, there may be mentioned dichloroethylenes, tetrachloroethane, trichloroethylene, perchloroethylene and oxides of carbon. The latter must be removed, for example, by means of a gas purge. These purges inevitably lead to losses of products which are moreover upgradable, such as ethylene not converted during the oxychlorination and which is recyclable. The formation of non-upgradable chlorinated by-products moreover requires their removal by incineration. The increase in the importance of this removal therefore further worsens the environmental impact of such a process.

The aim of the present invention is therefore to provide a process using ethylene with a purity of less than 99.8% which has the advantage of reducing the costs by abandoning complex separations for isolating the ethylene from the other products of cracking which are of no benefit for the manufacture of DCE, and which has the advantage of avoiding the abovementioned problems linked to the presence of acetylene and thus of ensuring the good operation of the chlorination and/or oxychlorination reactors.

To this effect, the invention relates to a process for the manufacture of DCE starting with a hydrocarbon source according to which:

a) the hydrocarbon source is subjected to a first cracking step, namely a pyrolysis step performed in a cracking oven, thus producing a mixture of cracking products;

b) the said mixture of cracking products is subjected to a succession of treatment steps ending with a drying step which makes it possible to obtain a mixture of products containing ethylene and other constituents;

c) the said mixture of products containing ethylene derived from step b) is separated into at least one fraction containing ethylene and into a heavy fraction;

d) the fraction(s) containing the ethylene is(are) conveyed to a chlorination reactor and/or an oxychlorination reactor, in which reactors most of the ethylene is converted to 1,2-dichloroethane;

e) the DCE obtained is separated from the streams of products derived from the chlorination and oxychlorination reactors;

the process being characterized in that a step for hydrogenating the acetylene is carried out upstream of the drying step ending the succession of treatment steps constituting step b) and/or on at least one of the fractions containing ethylene after separation during step c).

The expression "the process being characterized in that a step for hydrogenating the acetylene is carried out upstream of the drying step ending the succession of treatment steps constituting step b) and/or on at least one of the fractions containing ethylene after separation during step c)" is understood to mean that a step for hydrogenating the acetylene is carried out upstream of the drying step ending the succession of treatment steps constituting step b), on at least one of the fractions containing ethylene after separation during step c) or upstream of the drying step ending the succession of treatment steps constituting step b) and on at least one of the fractions containing ethylene after separation during step c).

The hydrocarbon source considered may be any known hydrocarbon source. Preferably, the hydrocarbon source subjected to cracking (step a)) is chosen from the group consisting of naphtha, gas oil, natural gas liquid, ethane, propane, butane, isobutane and mixtures thereof. In a particularly preferred manner, the hydrocarbon source is chosen from the group consisting of ethane, propane and propane/butane mixtures. Good results were obtained with a hydrocarbon source chosen from the group consisting of propane and propane/butane mixtures. The propane/butane mixtures may exist as such or may consist of mixtures of propane and butane.

The expression ethane, propane, butane and propane/butane mixtures is understood to mean, for the purposes of the present invention, products that are commercially available, namely that consist mainly of the pure product (ethane, propane, butane or propane/butane as a mixture) and secondarily of other saturated or unsaturated hydrocarbons, which are lighter or heavier than the pure product itself.

The expression first cracking step, namely a pyrolysis step performed in a cracking oven (step a)), is understood to mean a conversion, under the action of heat, of the hydrocarbon source in the presence or absence of third compounds such as water, oxygen, a sulphur derivative and/or a catalyst. This step gives rise to the formation of a mixture of cracking products.

This mixture of cracking products advantageously comprises hydrogen, carbon monoxide, carbon dioxide, nitrogen, oxygen, hydrogen sulphide and other sulpho compounds, organo compounds comprising at least one carbon atom and water.

This first cracking step is followed by step b) consisting of a succession of treatment steps ending with a drying step; a succession of treatment steps which make it possible to obtain a mixture of products containing ethylene and other constituents. This succession of treatment steps advantageously comprises steps for thermal recovery of the heat of the cracked gases, optionally for organic quenching (optionally including heat recovery through a network of exchangers with intermediate fluids), for aqueous quenching, for removing most of the carbon dioxide and most of the sulpho compounds present or added, such as hydrogen sulphide, optionally for removing part of the hydrogen and/or the methane, optionally for removing the acetylene, optionally for intermediate drying and compression steps, and ends with a step for drying the mixture obtained.

In the process according to the invention, the step for hydrogenating the acetylene may be preceded by a heat conditioning step necessary to bring the supply for the hydrogenation under required conditions.

In the process according to the invention, the organic quenching step and the aqueous quenching step may optionally consist of a single step.

In the process according to the invention, the step for removing part of the hydrogen and/or the methane may be a single step or two separate steps. Preferably, this step is a single step. The hydrogen and/or the methane may be removed, for example, via a PSA (pressure swing adsorption) process or via a membrane process.

Advantageously, this mixture obtained after step b) is a mixture of products containing ethylene and other constituents comprising hydrogen, methane, compounds comprising from 2 to 7 carbon atoms, carbon monoxide, nitrogen and oxygen. The hydrogen, the methane and the compounds comprising from 2 to 7 carbon atoms other than acetylene are preferably present in an amount of at least 200 ppm by volume relative to the total volume of the said mixture of products. The carbon monoxide, the nitrogen, the oxygen and the acetylene may be present in an amount of less than 200 ppm by volume or in an amount of at least 200 ppm by volume relative to the total volume of the said mixture of products. Compounds containing more than 7 carbon atoms, carbon dioxide, hydrogen sulphide and other sulpho compounds and water may also be present in the abovementioned mixture of products in an amount of less than 200 ppm by volume relative to the total volume of the said mixture of products.

This mixture of products containing ethylene and other constituents is therefore advantageously obtained from the abovementioned mixture of cracking products, freed optionally of part of the hydrogen and/or methane, of most of the carbon dioxide, of most of the hydrogen sulphide and of other sulpho compounds, optionally of part of the acetylene, of most of the organic compounds containing more than 7 carbon atoms and of most of the water.

After step b) defined above, the mixture of products containing ethylene and other constituents is subjected to step c) which advantageously comprises a maximum of four, preferably a maximum of three separation steps in order to obtain the fraction or fractions containing ethylene.

According to the process according to the invention, the separation of the mixture of products containing acetylene and other constituents in step c) leads to the formation of at least one fraction containing ethylene, preferably of two fractions containing ethylene and, in a particularly preferred manner, of a fraction containing ethylene which is enriched with the compounds lighter than ethylene, called below fraction A and of a second fraction containing ethylene advantageously enriched with ethylene, called fraction B below and of a heavy fraction (fraction C).

According to the process according to the invention, fraction A is advantageously conveyed to the chlorination reactor and fraction B advantageously to the oxychlorination reactor, preferably after expansion with recovery of energy.

According to the process of the invention, the quantities defined below to characterize the fraction B and the fraction A are those before their respective entry into oxychlorination and into chlorination.

Fraction B, after optionally removing the excess hydrogen used to hydrogenate the acetylene (case of the second subvariant of the second variant below), is advantageously characterized by a hydrogen content of less than or equal to 2%, preferably of less than or equal to 0.5% and in a particularly preferred manner of less than or equal to 0.1% by volume relative to the total volume of fraction B.

Fraction B is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction B.

Fraction B advantageously contains from 40% to 99.5% by volume of ethylene relative to the total volume of fraction B. Fraction B advantageously contains at least 40%, preferably at least 50% and in a particularly preferred manner at least 60% by volume of ethylene relative to the total volume of fraction B. Fraction B advantageously contains at most 99.5%, preferably at most 99.2% and in a particularly preferred manner at most 99% by volume of ethylene relative to the total volume of fraction B.

In the preferred case where the hydrocarbon source is ethane, fraction B advantageously comprises at least 60%, preferably at least 70% and in a particularly preferred manner at least 75% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

In the preferred case where the hydrocarbon source is a propane/butane mixture, fraction B advantageously comprises at least 40%, preferably at least 50% and in a particularly preferred manner at least 60% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

Fraction B, after hydrogenation of the acetylene, is additionally characterized by an acetylene content which is advantageously less than or equal to 0.01%, preferably less than or equal to 0.005% and in a particularly preferred manner less than or equal to 0.001% by volume relative to the total volume of fraction B.

Fraction A is advantageously enriched with compounds which are lighter than ethylene. These compounds are generally methane, nitrogen, oxygen, hydrogen and carbon monoxide. Advantageously, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.97% and in a particularly preferred manner at most 99.95% of compounds lighter than ethylene which are contained in the mixture of products subjected to step b).

In the preferred case where the hydrocarbon source is ethane, fraction A contains at least 90%, preferably at least 95% and in a particularly preferred manner at least 98% of compounds lighter than ethylene which are contained in the mixture of products subjected to step b). Advantageously, fraction A contains at most 99.99%, preferably at most 99.98% and in a particularly preferred manner at most 99.97% of compounds lighter than ethylene which are contained in the mixture of products subjected to step b).

In the preferred case where the hydrocarbon source is a propane/butane mixture, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.95% and in a particularly preferred manner at most 99.9% of compounds lighter than ethylene which are contained in the mixture of products subjected to step b).

Fraction A is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction A.

Fraction A advantageously contains a content by volume of ethylene such that it represents from 10% to 90% of the content by volume of ethylene of fraction B. Fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

In the preferred case where the hydrocarbon source is ethane, fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 15%, preferably at least 20% and in a particularly preferred manner at least 22% of the content by volume of ethylene of fraction B.

In the preferred case where the hydrocarbon source is a propane/butane mixture, fraction A advantageously contains a content by volume of ethylene such that it is less than or equal to 80%, preferably less than or equal to 75% and in a particularly preferred manner less than or equal to 70% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

Fraction A, after hydrogenation of the acetylene, is additionally characterized by an acetylene content which is advantageously less than or equal to 0.01%, preferably less than or equal to 0.005% and in a particularly preferred manner less than or equal to 0.001% by volume relative to the total volume of fraction A.

According to a first embodiment of the process according to the invention, considering that the process for the manufacture of DCE is advantageously balanced (that is to say that the process of manufacture by chlorination and oxychlorination of ethylene and pyrolysis of the 1,2-dichloroethane (DCE) formed makes it possible to generate the quantity of HCl necessary for the process), the fraction by weight of the ethylene throughput in each of fractions A and B is advantageously between 45 and 55% of the total quantity of ethylene produced (fraction A+fraction B). Preferably, the fraction by weight of the throughput of ethylene in fraction A is of the order of 55% and the fraction by weight of the throughput of ethylene in fraction B is of the order of 45% of the total quantity produced. In a particularly preferred manner, the fraction by weight of the throughput of ethylene in fraction A is of the order of 52.5% and the fraction by weight of the throughput of ethylene in fraction B is of the order of 47.5% of the total quantity produced.

According to a second embodiment of the process according to the invention, considering that the process for the manufacture of DCE is advantageously unbalanced (that is to say for example that an external source of HCl makes it possible to provide part of the supply of HCl for the oxychlorination or that a fraction of the DCE produced is not subjected to pyrolysis), the fraction by weight of the throughput of ethylene in each of fractions A and B is advantageously between 20 and 80% of the total quantity of ethylene produced (fraction A+fraction B). Preferably, the fraction by weight of the throughput of ethylene in fraction A is between 25 and 75% of the total quantity of ethylene produced (fraction A+fraction B).

According to a first variant of the second embodiment of the process according to the invention, considering that the process for the manufacture of DCE is advantageously unbalanced by an external source of HCl, the fraction by mole of the throughput of ethylene in fraction A is advantageously between 45 and 55%, preferably between 50 and 54% and in a particularly preferred manner of the order of 52.5% of the difference between the total molar quantity of ethylene contained in the mixture of products subjected to step b) and the molar quantity of HCl of the external source.

According to a second variant of the second embodiment of the process according to the invention, considering that the process for the manufacture of DCE is advantageously unbalanced by a co-production of DCE (some of the DCE is therefore not subjected to pyrolysis), the fraction by mole of the throughput of ethylene in fraction B is advantageously between 45 and 55%, preferably between 46 and 50% and in a particularly preferred manner of the order of 47.5% of the difference between the total molar quantity of ethylene contained in the mixture of products subjected to step b) and the molar quantity of DCE co-produced.

During step c), the mixture of products containing ethylene and other constituents derived from step b) is separated into at least one fraction containing ethylene and into a heavy fraction (fraction C). Fraction C advantageously contains ethane and compounds comprising at least 3 carbon atoms. Advantageously, these compounds comprising at least 3 carbon atoms result from the mixture of products containing ethylene and other constituents derived from step b) or are generated by side reactions during step c). Among the compounds comprising at least 3 carbon atoms, there may be mentioned propane, propene, butanes and their unsaturated derivatives as well as all the saturated or unsaturated heavier compounds.

Any separation process may be used to separate the said mixture of products containing ethylene into fraction A, fraction B and fraction C provided that it advantageously comprises a maximum of four, preferably a maximum of three separation steps in order to obtain the two fractions A and B.

According to a first preferred mode of separation, the mixture of products containing ethylene derived from step b) is subjected to a first separation step which makes it possible to extract fraction C therefrom and the resulting mixture is then subjected to a second separation step into fraction A and fraction B.

According to a second preferred mode of separation, the mixture of products containing ethylene derived from step b) is subjected to a first separation step which makes it possible to extract fraction A therefrom and the resulting mixture is then subjected to a second separation step into fraction B and fraction C.

The first mode of separation is particularly preferred. Numerous variants can make it possible to carry out this first particularly preferred mode of separation of the mixture of products containing ethylene derived from step a).

A preferred variant of the first mode of separation consists in subjecting the said mixture to a first separation step aimed at extracting fraction C and then in subjecting the resulting mixture to a second step for separating into fraction A and fraction B which are both distillation steps carried out by means of a distillation column equipped with associated auxiliary equipment such as at least one reboiler and at least one condenser.

According to this preferred variant of the first mode of separation, fraction C leaves advantageously at the bottom of the first distillation column, fraction A leaves at the top of the second distillation column and fraction B at the bottom of the second distillation column.

The distillation column may be chosen from plate distillation columns, packed distillation columns, distillation columns with structured packing and distillation columns combining two or more of the abovementioned internals.

According to a first variant of the process according to the invention, the process for the manufacture of DCE according to the invention is characterized in that an acetylene hydrogenation step is performed upstream of the drying step ending step b).

The expression "upstream of the drying step" is understood to mean that the hydrogenation step precedes the drying step with optionally at least one step between them.

The acetylene hydrogenation step may be carried out at any stage in the succession of treatment steps constituting step b) provided that it is performed before the drying step ending step b).

Preferably, according to this first variant of the process according to the invention, the acetylene hydrogenation step is performed downstream of the step for removing hydrogen sulphide and other sulpho compounds.

In a particularly preferred manner, according to this first variant of the process according to the invention, the acetylene hydrogenation step, optionally followed by at least one compression step and then by a step for removing part of the hydrogen and/or the methane, precedes the drying step terminating step b).

In a most particularly preferred manner, according to this first variant of the process according to the invention, the acetylene hydrogenation step, performed downstream of the step for removing hydrogen sulphide and the other sulpho compounds and optionally followed by at least one compression step and then by a step for removing part of the hydrogen and/or the methane, precedes the drying step ending step b).

According to this first variant, the acetylene hydrogenation step is advantageously preceded by the succession of treatment steps consisting, without limitation as for their order, of the steps for thermal recovery of the heat of the cracked gases, optionally for organic quenching, for aqueous quenching, for compression, for removing most of the carbon dioxide, for removing most of the hydrogen sulphide and the other sulpho compounds, optionally for removing part of the hydrogen and/or the methane and optionally for intermediate drying.

According to a first subvariant of the first variant, the acetylene hydrogenation step is preferably preceded by the succession of treatment steps consisting, in order, of at least one step for thermal recovery of the heat of the cracked gases, optionally at least one organic quenching step, at least one aqueous quenching step, at least one compression step, at least one step for removing most of the carbon dioxide and at least one step for removing most of the hydrogen sulphide and the other sulpho compounds.

According to this first subvariant of the first variant, the acetylene hydrogenation step is, in a particularly preferred manner, preceded by the succession of treatment steps consisting, in order, of a step for thermal recovery of the heat of the cracked gases, optionally an organic quenching step, an aqueous quenching step, several compression steps (preferably less than 5 in number, in a particularly preferred manner from 3 to 4 in number, in a most particularly preferred manner 3 in number) and a step for removing most of the carbon dioxide combined with a step for removing most of the hydrogen sulphide and the other sulpho compounds.

According to this first subvariant of the first variant, the succession of treatment steps constituting step b) therefore, in a most particularly preferred manner, consists, in order, of a step for thermal recovery of the heat of the cracked gases, optionally an organic quenching step, an aqueous quenching step, several compression steps (preferably less than 5 in number, in a particularly preferred manner from 3 to 4 in number, in a most particularly preferred manner 3 in number), a step for removing most of the carbon dioxide combined with a step for removing most of the hydrogen sulphide and the other sulpho compounds, the acetylene hydrogenation step, at least one (preferably one) compression step, a step for removing part of the hydrogen and/or the methane and the drying step ending step b).

According to a second subvariant of the first variant, the acetylene hydrogenation step is preferably preceded by the succession of treatment steps consisting, in order, of at least one step for thermal recovery of the heat of the cracked gases, optionally at least one organic quenching step, at least one aqueous quenching step, at least one compression step, at least one step for removing most of the carbon dioxide, at least one step for removing most of the hydrogen sulphide and the other sulpho compounds and at least one compression step.

According to this second subvariant of the first variant, the acetylene hydrogenation step is, in a particularly preferred manner, preceded by the succession of treatment steps consisting, in order, of one step for thermal recovery of the heat of the cracked gases, optionally an organic quenching step, an aqueous quenching step, several compression steps (preferably less than 5 in number, in a particularly preferred manner from 3 to 4 in number, in a most particularly preferred manner 3 in number), a step for removing most of the carbon dioxide combined with a step for removing most of the hydrogen sulphide and the other sulpho compounds and at least one (preferably one) compression step.

According to this second subvariant of the first variant, the succession of treatment steps constituting step b) therefore, in a most particularly preferred manner, consists, in order, of a step for thermal recovery of the heat of the cracked gases, optionally an organic quenching step, an aqueous quenching step, several compression steps (preferably less than 5 in number, in a particularly preferred manner from 3 to 4 in number, in a most particularly preferred manner 3 in number), a step for removing most of the carbon dioxide combined with a step for removing most of the hydrogen sulphide and the other sulpho compounds, at least one (preferably one) compression step, the acetylene hydrogenation step, a step for removing part of the hydrogen and/or the methane and the drying step ending step b).

According to a first particular mode of this second subvariant, an intermediate drying step may be optionally carried out between the acetylene hydrogenation step and the step for removing part of the hydrogen and/or the methane.

According to a second particular mode of this second subvariant, an intermediate drying step may be optionally carried out between the compression step preceding the acetylene hydrogenation step and the acetylene hydrogenation step itself.

The second subvariant of the first variant of the process is preferred to the first subvariant.

According to a second variant, the process for the manufacture of DCE according to the invention is characterized in that an acetylene hydrogenation step is performed on at least one of the fractions containing ethylene after separation during step c).

According to a first subvariant of the second variant, the process for the manufacture of DCE according to the invention is characterized in that an acetylene hydrogenation step is advantageously performed on fraction A after separation during step c).

According to this first subvariant, the process for the manufacture of DCE according to the invention is optionally characterized by an additional drying step taking place directly after the hydrogenation step and before fraction A is conveyed to a chlorination reactor. Preferably, this additional drying step is carried out.

According to a second subvariant of the second variant, the process for the manufacture of DCE according to the invention is characterized in that the acetylene hydrogenation step is advantageously performed on fraction B) after separation during step c).

According to this second subvariant, the process for the manufacture of DCE according to the invention is optionally characterized by a step for removing the excess hydrogen used to hydrogenate the acetylene. Preferably, this hydrogen removal step is carried out.

According to a third subvariant of the second variant, the process for the manufacture of DCE according to the invention is characterized in that an acetylene hydrogenation step is advantageously carried out on fraction A and on fraction B after separation during step c). The specific characteristics defined above for the first and second subvariants also apply to the case of the third subvariant.

According to a third variant, the process for the manufacture of DCE according to the invention is characterized in that an acetylene hydrogenation step is performed upstream of the drying step ending step b) and on at least one of the fractions containing ethylene after separation during step c).

The specific characteristics defined above for the first and second variants also apply to the third variant.

According to the process of the invention, the first and second variants are preferred. The first variant is particularly preferred with an ultimate preference for its second subvariant.

The acetylene hydrogenation step may be carried out by means of any known hydrogenation catalyst such as, for example, catalysts based on palladium, platinum, rhodium, ruthenium or iridium placed on a support such as alumina, silica, silica/alumina, carbon, calcium carbonate or barium sulphate, but also catalysts based on nickel and those based on the cobalt-molybdenum complex.

Preferably, the hydrogenation step is performed by means of a catalyst based on palladium or platinum. In a particularly preferred manner, it is performed by means of a catalyst based on palladium.

As regards the support, the hydrogenation step is performed by means of a catalyst based on the abovementioned compounds (preferably palladium or platinum, in a particularly preferred manner palladium), preferably deposited on alumina, carbon, calcium carbonate or barium sulphate.

The quantity of palladium in the catalyst is advantageously of the order of 1% by weight.

The temperature at which the acetylene hydrogenation step is then carried out is advantageously at least 5° C., preferably at least 20° C., in a particularly preferred manner at least 25° C., in a most particularly preferred manner at least 40° C. and in a truly most particularly preferred manner at least 50° C. It is advantageously at most 150° C., preferably at most 120° C. and in a particularly preferred manner at most 100° C.

As regards the pressure, it is advantageously greater than or equal to 1, preferably greater than or equal to 5, in a particularly preferred manner greater than or equal to 10, in a most particularly preferred manner greater than or equal to 15 bar and in a truly most particularly preferred manner greater than or equal to 25 bar. It is advantageously less than or equal to 50, preferably less than or equal to 45, in a particularly preferred manner less than or equal to 40 and in a most particularly preferred manner less than or equal to 30 bar.

Advantageously, the hydrogenation of the acetylene is carried out using quantities of hydrogen such that its hydrogenation is complete, that is to say preferably at least 99%, even if this is accompanied by a hydrogenation of part of the ethylene to ethane. The latter is then advantageously conveyed to the first cracking step. The quantity of hydrogen is advantageously such that the hydrogen:acetylene molar ratio is equal to or greater than 1, preferably equal to or greater than 1.5, in a particularly preferred manner equal to or greater than 2, in a most particularly preferred manner equal to or greater than 3 and in a truly most particularly preferred manner equal to 4.

The hydrogen necessary for the acetylene hydrogenation step may be the hydrogen present in the medium or hydrogen added thereto. In the latter case, the hydrogen is advantageously purified beforehand so as to be compatible with the hydrogenation of the acetylene, in particular the mercury which may be present is removed therefrom by any known means.

In the case where the hydrogenation is carried out upstream of the drying step and on fraction A, the hydrogen necessary is preferably the hydrogen present in the medium. In the case where the hydrogenation is carried out on fraction B, the hydrogen necessary is preferably the hydrogen added to the medium. In the latter case, the operation is carried out in a particularly preferred manner with a slight excess of hydrogen. The potential excess hydrogen is in a most particularly preferred manner removed before fraction B is conveyed to the oxychlorination reactor. In the latter case, the hydrogen may be removed by a PSA process or via a membrane process, preferably by a PSA process.

The chlorination reaction is advantageously performed in a liquid phase (preferably mainly DCE) containing a dissolved catalyst such as $FeCl_3$ or another Lewis acid. It is possible to advantageously combine this catalyst with cocatalysts such as alkali metal chlorides. A pair which has given good results is the complex of $FeCl_3$ with LiCl (lithium tetrachloroferrate—as described in patent application NL 6901398).

The quantities of $FeCl_3$ advantageously used are of the order of 1 to 10 g of $FeCl_3$ per kg of liquid stock. The molar ratio of $FeCl_3$ to LiCl is advantageously of the order of 0.5 to 2.

The chlorination process according to the invention is advantageously performed at temperatures of between 30 and 150° C. Good results were obtained regardless of the pressure both at a temperature less than the boiling temperature (under-cooled chlorination) and at the boiling temperature itself (boiling chlorination).

When the chlorination process according to the invention is a under-cooled chlorination, it gave good results by operating at a temperature which is advantageously greater than or equal to 50° C. and preferably greater than or equal to 60° C., but advantageously less than or equal to 80° C. and preferably less than or equal to 70° C.; with a pressure in the gaseous phase advantageously greater than or equal to 1.5 and preferably greater than or equal to 2 absolute bar, but advantageously less than or equal to 20, preferably less than or equal to 10 and in a particularly preferred manner less than or equal to 6 absolute bar.

A boiling chlorination process is particularly preferred which makes it possible, where appropriate, to usefully recover the heat of reaction. In this case, the reaction advantageously takes place at a temperature greater than or equal to 60° C., preferably greater than or equal to 90° C. and in a particularly preferred manner greater than or equal to 95° C. but advantageously less than or equal to 150° C. and preferably less than or equal to 135° C.; with a pressure in the gaseous phase advantageously greater than or equal to 0.2, preferably greater than or equal to 0.5, in a particularly preferred manner greater than or equal to 1.2 and in a most particularly preferred manner greater than or equal to 1.5 absolute bar but advantageously less than or equal to 10 and preferably less than or equal to 6 absolute bar.

The chlorination process may also be a loop under-cooled boiling mixed chlorination process. The expression loop under-cooled boiling mixed chlorination process is understood to mean a process in which cooling of the reaction medium is performed, for example, by means of an exchanger immersed in the reaction medium or by a loop circulating in an exchanger, while producing in a gaseous phase at least the quantity of DCE formed. Advantageously, the reaction temperature and pressure are adjusted for the DCE produced to leave in the gaseous phase and to remove the remainder of the calories from the reaction medium by means of the exchange surface.

In addition, the chlorination process is advantageously performed in a chlorinated organic liquid medium. Preferably, this chlorinated organic liquid medium, also called liquid stock, mainly consists of DCE.

The fraction A containing the ethylene and the chlorine (itself pure or diluted) may be introduced by any known device into the reaction medium together or separately. A separate introduction of the fraction A may be advantageous in order to increase its partial pressure and facilitate its dissolution which often constitutes a limiting step of the process.

The chlorine is added in a sufficient quantity to convert most of the ethylene and without requiring the addition of an excess of unconverted chlorine. The chlorine/ethylene ratio used is preferably between 1.2 and 0.8 and in a particularly preferred manner between 1.05 and 0.95 mol/mol.

The chlorinated products obtained contain mainly DCE and small quantities of by-products such as 1,1,2-trichloroethane or small quantities of chlorination products of ethane or methane. The separation of the DCE obtained from the stream of products derived from the chlorination reactor is carried out according to known modes and makes it possible in general to exploit the heat of the chlorination reaction.

The unconverted products (methane, carbon monoxide, nitrogen, oxygen and hydrogen) are then subjected to an easier separation than what would have been necessary to separate pure ethylene starting with the initial mixture.

The oxychlorination reaction is advantageously performed in the presence of a catalyst comprising active elements including copper deposited on an inert support. The inert support is advantageously chosen from alumina, silica gels, mixed oxides, clays and other supports of natural origin. Alumina constitutes a preferred inert support.

Catalysts comprising active elements which are advantageously at least two in number, one of which is copper, are preferred. Among the active elements other than copper, there may be mentioned alkali metals, alkaline-earth metals, rare-earth metals and metals of the group consisting of ruthenium, rhodium, palladium, osmium, iridium, platinum and gold. The catalysts containing the following active elements are particularly advantageous: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in patent applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and in a particularly preferred manner between 50 and 70 g/kg of catalyst.

The magnesium content, calculated in metal form, is advantageously between 10 and 30 g/kg, preferably between 12 and 25 g/kg and in a particularly preferred manner between 15 and 20 g/kg of catalyst.

The alkali metal content, calculated in metal form, is advantageously between 0.1 and 30 g/kg, preferably between 0.5 and 20 g/kg and in a particularly preferred manner between 1 and 15 g/kg of catalyst.

The Cu:Mg:alkali metal(s) atomic ratios are advantageously 1:0.1-2:0.05-2, preferably 1:0.2-1.5:0.1-1.5 and in a particularly preferred manner 1:0.5-1:0.15-1.

Catalysts having a specific surface area, measured according to the B.E.T. method with nitrogen, advantageously between 25 m$^2$/g and 300 m$^2$/g, preferably between 50 and 200 m$^2$/g and in a particularly preferred manner between 75 and 175 m$^2$/g, are particularly advantageous.

The catalyst may be used in a fixed bed or in a fluidized bed. This second option is preferred. The oxychlorination process is exploited under the range of the conditions usually recommended for this reaction. The temperature is advantageously between 150 and 300° C., preferably between 200 and 275° C. and most preferably from 215 to 255° C. The pressure is advantageously greater than atmospheric pressure. Values of between 2 and 10 absolute bar gave good results. The range between 4 and 7 absolute bar is preferred. This pressure may be usefully modulated in order to obtain an optimum residence time in the reactor and to maintain a constant rate of passage for various speeds of operation. The usual residence times range from 1 to 60 seconds and preferably from 10 to 40 seconds.

The source of oxygen for this oxychlorination may be air, pure oxygen or a mixture thereof, preferably pure oxygen. The latter solution, which allows easy recycling of the unconverted reagents, is preferred.

The reagents may be introduced into the bed by any known device. It is generally advantageous to introduce the oxygen separately from the other reagents for safety reasons. These also require maintaining the gaseous mixture leaving the reactor or recycled thereto outside the limits of inflammability at the pressures and temperatures considered. It is preferable to maintain a so-called rich mixture, that is containing too little oxygen relative to the fuel to ignite. In this regard, the abundant presence (>2%, preferably >5% vol) of hydrogen would constitute a disadvantage given the wide range of inflammability of this compound.

The hydrogen chloride/oxygen ratio used is advantageously between 2 and 6 mol/mol. The ethylene/hydrogen chloride ratio is advantageously between 0.4 and 0.6 mol/mol.

The chlorinated products obtained contain mainly DCE and small quantities of by-products such as 1,1,2-trichloroethane. The separation of the DCE obtained from the stream of products derived from the oxychlorination reactor is carried out according to known modes. The heat of the oxychlorination reaction is generally recovered in vapour form which can be used for the separations or for any other purpose.

The unconverted products such as methane and ethane are then subjected to an easier separation than that which would have been necessary to separate pure ethylene starting from the initial mixture.

The DCE obtained is then separated from the streams of products derived from the chlorination and oxychlorination reactors and conveyed to the pyrolysis oven so as to be advantageously converted to VC therein.

The invention therefore also relates to a process for the manufacture of VC. To this effect, the invention relates to a process for the manufacture of VC, characterized in that the DCE obtained by the process according to the invention is converted to VC in the pyrolysis oven.

The conditions under which the pyrolysis may be carried out are known to persons skilled in the art. This pyrolysis is advantageously obtained by a reaction in the gaseous phase in a tubular oven. The usual pyrolysis temperatures are between 400 and 600° C. with a preference for the range between 480° C. and 540° C. The residence time is advantageously between 1 and 60 s with a preference for the range from 5 to 25 s. The rate of conversion of the DCE is advantageously limited to 45 to 75% in order to limit the formation of by-products and the fouling of the tubes of the oven. The following steps make it possible, using any known device, to collect the purified VC and the hydrogen chloride to be upgraded preferably to the oxychlorination. Following purification, the unconverted DCE is advantageously conveyed to the pyrolysis oven.

In addition, the invention also relates to a process for the manufacture of PVC. To this effect, the invention relates to a process for the manufacture of PVC by polymerization of the VC obtained by the process according to the invention.

The process for the manufacture of PVC may be a mass, solution or aqueous dispersion polymerization process, preferably it is an aqueous dispersion polymerization process.

The expression aqueous dispersion polymerization is understood to mean free radical polymerization in aqueous suspension as well as free radical polymerization in aqueous emulsion and polymerization in aqueous microsuspension.

The expression free radical polymerization in aqueous suspension is understood to mean any free radical polymerization process performed in aqueous medium in the presence of dispersing agents and oil-soluble free radical initiators.

The expression free radical polymerization in aqueous emulsion is understood to mean any free radical polymerization process performed in aqueous medium in the presence of emulsifying agents and water-soluble free radical initiators.

The expression aqueous microsuspension polymerization, also called polymerization in homogenized aqueous dispersion, is understood to mean any free radical polymerization process in which oil-soluble initiators are used and an emulsion of droplets of monomers is prepared by virtue of a powerful mechanical stirring and the presence of emulsifying agents.

The process according to the invention therefore has the advantage of avoiding the problems linked to the presence of acetylene during the chlorination and oxychlorination reactions such as the formation of non-upgradable by-products contributing to soiling the equipment which puts a strain on the yield of the chlorination/oxychlorination reactions. It also allows a lower consumption of the reagents which are chlorine and hydrogen chloride and makes it possible to limit the purges of oxides of carbon and consequently the losses of upgradable products. Finally, it has the advantage of limiting the incineration of the chlorinated organic compounds.

A final advantage of the process according to the invention is that it makes it possible to have, on the same industrial site, a completely integrated process from the hydrocarbon source to the polymer obtained starting with the monomer manufactured.

BRIEF DESCRIPTION OF DRAWING

The process according to the invention will now be illustrated with reference to the drawing accompanying the present description. This drawing consists of the appended FIG. 1, schematically representing one embodiment of the second subvariant of the preferred first variant of the process for the manufacture of DCE according to the invention.

The hydrocarbon source 1 is subjected to a pyrolysis step in a cracking oven 2 thus producing a mixture of cracking products 3. The latter is subjected to a succession of treatment steps consisting of a step for thermal recovery of the heat of the cracked gases 4, optionally an organic quenching step 5, an aqueous quenching step 6, three compression steps 7, a step for removing most of the carbon dioxide combined with a step for removing most of the hydrogen sulphide and the other sulpho compounds 8, a compression step 9, the acetylene hydrogenation step 10, a step for removing part of the hydrogen and/or the methane 11 and the drying step 12.

Figure 1:
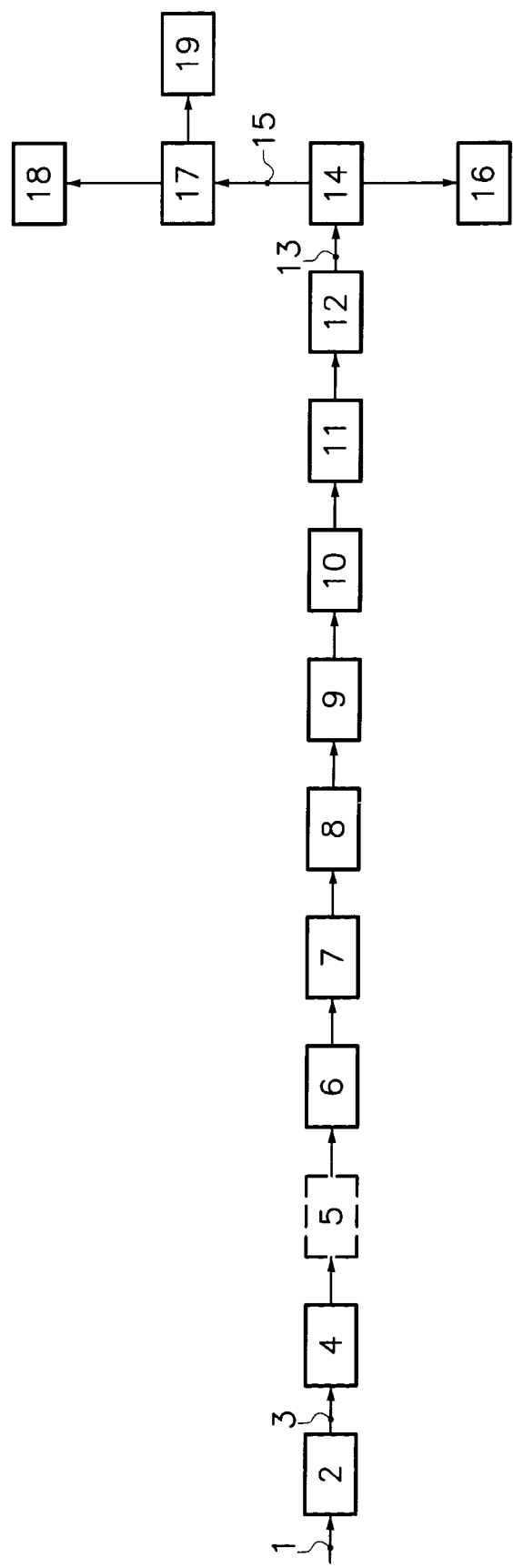

The resulting mixture containing ethylene and other constituents 13 is subjected to a first step for separating 14 into two different fractions, namely fraction 15 and fraction 16. Fraction 15 is then subjected to a second step for separating 17 into fraction 18 and fraction 19.

Fraction 18, enriched with compounds lighter than ethylene, in particular methane, hydrogen, nitrogen, oxygen and carbon monoxide, is conveyed to the ethylene chlorination unit.

Fraction 19 which is characterized by a lower hydrogen content is conveyed to the ethylene oxychlorination unit.

Fraction 16 may be conveyed, completely or in part, to the cracking oven 2 as raw material or as fuel.

The invention claimed is:

1. A process for the manufacture of 1,2-dichloroethane starting with a hydrocarbon source, wherein:
   a) the hydrocarbon source is subjected to a cracking producing a mixture of cracking products comprising ethylene and acetylene;
   b) the mixture of cracking products is subjected to a succession of treatments ending with drying, which provides a mixture of products comprising ethylene and other constituents;
   c) the mixture of products comprising ethylene and other constituents is separated into at least one fraction comprising ethylene and into a heavy fraction;
   d) the fraction(s) comprising the ethylene in c) is (are) conveyed to a chlorination reactor and/or an oxychlorination reactor, in which reactors most of the ethylene is converted to 1,2-dichloroethane; and
   e) the 1,2-dichloroethane obtained in d) is separated from products derived from the chlorination and/or oxychlorination reactors;

wherein the acetylene is hydrogenated upstream of the drying in b), and/or wherein hydrogenating is performed on at least one of the fractions comprising ethylene obtained in c) before being conveyed to a chlorination reactor and/or an oxychlorination reactor in d).

2. The process for the manufacture of 1,2-dichloroethane according to claim 1, wherein the hydrocarbon source is chosen from the group consisting of naphtha, gas oil, natural gas liquid, ethane, propane, butane, isobutane and mixtures thereof.

3. The process for the manufacture of 1,2-dichloroethane according to claim 1, wherein the hydrocarbon source is chosen from the group consisting of ethane, propane, butane and propane/butane mixtures.

4. The process according to claim 1, wherein the acetylene is hydrogenated upstream of the drying in b).

5. The process for the manufacture of 1,2-dichloroethane according to claim 1, wherein the acetylene hydrogenation is performed in the presence of a catalyst comprising palladium.

6. The process according to claim 1, wherein the mixture of products comprising ethylene and other constituents in b) comprises ethylene, hydrogen, methane, compounds comprising from 2 to 7 carbon atoms, carbon monoxide, nitrogen and oxygen.

7. The process according to claim 1, wherein the separation of the mixture of products comprising ethylene and other constituents in c) provides a fraction enriched with compounds lighter than ethylene comprising part of the ethylene (fraction A), of a fraction enriched with ethylene (fraction B) and said heavy fraction (fraction C).

8. The process according to claim 7, wherein fraction B comprises from 40% to 99.5% by volume of ethylene relative to the total volume of fraction B.

9. The process according to claim 7, wherein fraction A comprises a content by volume of ethylene such that it represents from 10% to 90% of the content by volume of ethylene of fraction B.

10. A process for the manufacture of vinyl chloride, wherein the 1,2-dichloroethane obtained by the process according to claim 1 is converted to vinyl chloride in a pyrolysis oven.

11. A process for the manufacture of polyvinyl chloride by polymerization of the vinyl chloride obtained by the process according to claim 10.

12. The process for the manufacture of 1,2-dichloroethane according to claim 4, wherein the succession of treatments constituting b) consists, in order, of thermal recovery of the heat of the cracked gases, optionally and organic quenching, an aqueous quenching, plural compressions, removing most of any carbon dioxide combined with removing most of any hydrogen sulphide and any other sulpho compounds, at Least one compression, the acetylene hydrogenation, removing part of any hydrogen and/or any methane and the drying ending b).

13. The process according to claim 1, wherein hydrogenating is performed on at least one of the fractions comprising ethylene obtained in c) before being conveyed to a chlorination reactor and/or an oxychlorination reactor in d).

14. The process according to claim 1, wherein the acetylene is hydrogenated upstream of the drying in b), and wherein hydrogenating is performed on at least one of the fractions comprising ethylene obtained in c) before being conveyed to a chlorination reactor and/or an oxychlorination reactor in d).

15. The process according to claim 7, wherein fraction C comprises ethane and compounds of at least 3 carbon atoms.

16. The process according to claim 7, wherein fraction A is conveyed to the chlorination reactor and fraction B is conveyed to the oxychlorination reactor.

* * * * *